(12) United States Patent
Elwell et al.

(10) Patent No.: US 7,829,340 B2
(45) Date of Patent: Nov. 9, 2010

(54) ORAL FLUID ASSAYS FOR THE DETECTION OF HEAVY METAL EXPOSURE

(75) Inventors: Eugene E. Elwell, Mt. Laurel, NJ (US); Robyn Hannigan, Jonesboro, AR (US); Edward Eckert, Hadden Heights, NJ (US)

(73) Assignee: OFT Labs, LLC, Mount Laurel, NJ (US)

( * ) Notice: Subject to any disclaimer, the term of this patent is extended or adjusted under 35 U.S.C. 154(b) by 0 days.

(21) Appl. No.: 12/180,717

(22) Filed: Jul. 28, 2008

(65) Prior Publication Data

US 2009/0038380 A1 Feb. 12, 2009

Related U.S. Application Data

(60) Provisional application No. 60/954,209, filed on Aug. 6, 2007.

(51) Int. Cl.
G01N 33/20 (2006.01)
G01N 33/48 (2006.01)

(52) U.S. Cl. .............................. 436/77; 436/63; 436/73; 436/74; 436/173; 422/68.1; 422/69

(58) Field of Classification Search .................. 436/63, 436/73, 74, 77, 81, 83, 173, 178; 422/61, 422/68.1, 69, 101; 250/281, 282

See application file for complete search history.

(56) References Cited

U.S. PATENT DOCUMENTS

| | | | |
|---|---|---|---|
| 4,853,325 | A | 8/1989 | Vodian et al. |
| 5,056,521 | A | 10/1991 | Parsons |
| 5,609,160 | A | 3/1997 | Bahl et al. |
| 5,714,341 | A | 2/1998 | Thieme et al. |
| 5,981,300 | A | 11/1999 | Moll et al. |
| 6,494,856 | B1 | 12/2002 | Zygmont |
| 6,518,785 | B2 | 2/2003 | Sasaki |
| 7,192,555 | B2 | 3/2007 | Mink et al. |
| 7,221,861 | B1 | 5/2007 | Hannigan et al. |
| 7,393,691 | B2 | 7/2008 | Farquharson et al. |
| 2003/0108846 | A1* | 6/2003 | Hoertsch .................... 433/216 |
| 2005/0010132 | A1* | 1/2005 | Pestes et al. ................. 600/572 |
| 2005/0079629 | A1 | 4/2005 | Guo et al. |
| 2008/0173806 | A1 | 7/2008 | Schneider |
| 2009/0043226 | A1 | 2/2009 | Elwell |

FOREIGN PATENT DOCUMENTS

| | | |
|---|---|---|
| KR | 1992-0009425 B1 | 10/1992 |
| KR | 10-0333517 B1 | 4/2002 |
| WO | WO 88/08137 A1 | 10/1988 |

OTHER PUBLICATIONS

"DNA Self Collection Kit for In Home Paternity Tests." Beta Paternity. 2006. Published Jun. 24, 2006. <http://web.archive.org/web/20060624173126/http://www.betagenics.com/kit/self-collection-swabs.html>.
PCT/US2008/071309 International Search Report dated Jan. 23, 2009.
PCT/US2008/071318 International Search Report dated Jan. 23, 2009.
Barbosa, F. et al., "A Critical Review of Biomarkers Used for Monitoring Human Exposure to Lead: Advantages, Limitations, and Future Needs," (2005) Environ. Health Perspect. 113:1669-74.
Barbosa, F. et al., "Evaluation of the use of salivary lead levels as a surrogate of blood lead or plasma lead levels in lead exposed objects," (2006) Arch. Toxicol. 80:633-7.
Thaweboon, S. et al., "Lead in saliva and its relationship to blood in the residents of Klity Village in Thailand," (2005) Southeast Asian J. Trop. Med. Public Health. 36:1576-9.
Koh, D. et al., "Can salivary lead be used for biological monitoring of lead exposed individuals?" (2003) Occup. Environ Med. 60:696-8.
Nriagu, J. et al., "Lead levels in blood and saliva in a low-income population of Detroit, Michigan," (2006) Int. J. Hyg. Environ. Health. 209:109-121.
Nevin, R., Lead Exposure Study, "Research Links Childhood Lead Exposure to Changes in Violent Crime Rates Throughout the 20th Century," Environmental Research, May 2000.
Mangla, A.T. et al., "The Correlation of Same-Visit Saliva Tests with Laboratory-Based Measurements," Poster and Abstract presented on Jun. 27, 2007.

* cited by examiner

*Primary Examiner*—Maureen M Wallenhorst
(74) *Attorney, Agent, or Firm*—Woodcock Washburn, LLP

(57) ABSTRACT

Methods for measuring the concentration of heavy metals such as lead in oral fluid are provided. The concentration of lead in oral fluid can be accurately correlated with the concentration of lead in the blood serum. The methods are useful for, among other things, diagnosis and monitoring of heavy metal exposure.

27 Claims, 2 Drawing Sheets

ORAL FLUID ASSAYS FOR THE DETECTION OF HEAVY METAL EXPOSURE

CROSS-REFERENCE TO RELATED APPLICATIONS

This application claims priority of U.S. Provisional Application Ser. No. 60/954,209, filed Aug. 6, 2007, which is incorporated herein by reference in its entirety.

FIELD

This invention relates generally to the field of biomedical diagnostics. More specifically, the invention relates to methods for screening for exposure to metals and metalloids, which methods can be carried out noninvasively.

BACKGROUND

Various publications, including patents, published applications, technical articles and scholarly articles are cited throughout the specification. Each of these cited publications is incorporated by reference herein, in its entirety.

Exposure to certain metals and metalloids has been implicated in various ill effects on human and animal health. Such metals are often referred to as heavy metals or toxic metals, although these terms are often used inconsistently, and there is no standard or even consensus as to what characteristics classifies a metal as heavy or toxic. Nevertheless, even low levels of exposure to some of these metals has been associated with neurotoxicity, nephrotoxicity, teratogenicity, cancer, and the like.

Heavy metals are prevalent in all environments, and are present there both naturally and through human activity such as pollution. Exposure to such metals can be by way of ingestion of contaminated food or water, inhalation of contaminated air, by absorption through the skin or mucosal membranes, and the like. In many cases, even low level exposure can result in adverse health effects.

One particular metal, lead, remains a worldwide health concern, especially in children. There is increasing recognition that there is no safe level of lead exposure. Lead exposure is problematic for children because lead can accumulate in their nervous system, and can also readily cross their blood brain barrier, which is not fully developed. Stricter environmental regulation, particularly in developed countries, has significantly reduced lead exposure in children, although remnants of a bygone era such as lead-based paint, and lead-based plumbing, still prevalent in older and urban homes and businesses, are cause for many cases of lead-poisoning in the United States alone.

In developing nations, lead exposure and poisoning is a prevalent problem. This is because such nations, often having lax or non-existent environmental regulations, permit the continued sale and use of gasoline containing lead additives, lead-based paint, lead-based cosmetics such as lead-kohl, lead-plumbing, and lead-solder. Parts of South America, Sub-Saharan Africa, Asia, Eastern Europe, and the Middle East have persistent problems with lead-contamination of the environment.

The adverse effects of lead exposure are often not immediately apparent. Prolonged exposure, however, generally manifests itself in children by irritability, a loss of appetite and weight, pain, anemia, learning difficulty and disabilities, stunted growth, impaired hearing and low IQ, among other things. In adults, lead poisoning can manifest itself through pain and numbness in extremities, headaches, memory loss, mood disorders, and reduced sperm count. Rates of childhood lead exposure have also been linked to the rate of violent crime.

Many of the effects of lead exposure can be reversed with proper treatment, although many other effects, particularly the neurological effects, are irreversible. In general, more intense therapies are indicated for higher levels of exposure. A proper treatment regimen for lead exposure, however, depends on a proper diagnosis.

At the present time, lead exposure, including the level or extent of exposure, is usually diagnosed by assaying for the amount of lead in the blood. The invasive aspect of blood testing carries with it a general reluctance or unwillingness for people to get needed testing, which may in turn delay treatment, and they may thus risk irreversible damage. In addition, blood testing can be particularly traumatic for younger children, who are the most at risk for adverse health effects of lead exposure. Less invasive screening methods, then, are desired in order to secure greater compliance with lead testing protocols.

Common non-invasive screens for various diagnostics include the collection and analysis of other bodily fluids such as urine, saliva, and sputum. Avoiding blood analysis provides the additional advantage of increased safety for the investigator. With respect to diagnosis of toxic metal exposure, and more particularly with respect to diagnosis of lead exposure, such non-invasive screens have not met with success. Urinalysis, fecal analysis, hair analysis, and nail analysis, suffer from various shortfalls (Barbosa F et al. (2005) Environ. Health Perspect. 113:1669-74). With respect to saliva, variation in saliva production, saliva stimulation, lack of proper standards, absence of reliable reference values for human populations, and low levels of lead actually present in the saliva limit the utility of saliva in a determination of lead exposure. Indeed, several investigators have concluded that salivary lead is not suitable for determining lead exposure (see, e.g., Barbosa F et al. (2006) Arch. Toxicol. 80:633-7; Thaweboon S et al. (2005) Southeast Asian J. Trop. Med. Public Health. 36:1576-9; and, Koh D et al. (2003) Occup. Environ Med. 60:696-8). Some recent data, however, suggests a weak association between blood lead and saliva lead concentrations (Nriagu J et al. (2006) Int. J. Hyg. Environ. Health. 209:109-121). Nevertheless, to date, blood analysis remains the gold standard for proper detection and diagnosis of lead exposure and poisoning.

SUMMARY

The invention provides methods for assaying a subject for heavy metal exposure, and preferably for lead exposure. Generally, the methods comprise providing a sample of oral fluid from a subject, and measuring the concentration of said heavy metal present in said sample. The subject can be any animal, and is preferably a mammal, and more preferably a human. The heavy metal is preferably lead. Providing a sample of oral fluid can comprise providing a swab that comprises the subject's oral fluid. Providing a swab can comprise rubbing the swab along the vestibular aspect of the mandibular gumline of the subject. In some preferred aspects, the swab comprises a polymer of ethylene glycol and terephthalic acid.

The measuring step can utilize any suitable technique in the art such as inductively coupled plasma mass spectrometry, atomic absorption spectrometry, atomic emission spectroscopy, electrospray ionization tandem mass spectrometry, high performance liquid chromatography tandem mass spectrometry, inductively coupled plasma optical emission spectroscopy, or capillary zone electrophoresis mass spectrometry. In some aspects, the methods further comprise correlating the measured concentration of the heavy metal in the oral fluid sample with the blood serum concentration of said heavy metal in the subject. For example, the correlating step can comprise comparing the concentration measurement with reference values for no exposure to the heavy metal, low level of exposure to the heavy metal, moderate level of exposure to the heavy metal, or high level of exposure to the heavy metal. The measured values relative to the reference values indicate the level of the heavy metal in the blood of the subject. The concentration of heavy metal in the sample is preferably predictive of the amount of heavy metal in the blood of the subject with a confidence interval of greater than 90%.

The invention also features kits for practicing the inventive methods, for example, kits for assaying a subject for heavy metal exposure. In some aspects, the kits comprise a swab and instructions for using the kit in any of the inventive methods. The kits are preferably utilized for assaying for lead exposure.

The invention further provides systems for providing a quantitative assessment of heavy metal intoxication. Generally, the systems comprise a sample of oral fluid from a subject and means for measuring the amount of a heavy metal in the sample. The heavy metal is preferably lead. For example, the means for measuring the amount of a heavy metal such as lead in the sample can comprise inductively coupled plasma mass spectrometry, atomic absorption spectrometry, atomic emission spectroscopy, electrospray ionization tandem mass spectrometry, high performance liquid chromatography tandem mass spectrometry, inductively coupled plasma optical emission spectroscopy, or capillary zone electrophoresis mass spectrometry.

DETAILED DESCRIPTION

Figure 1:
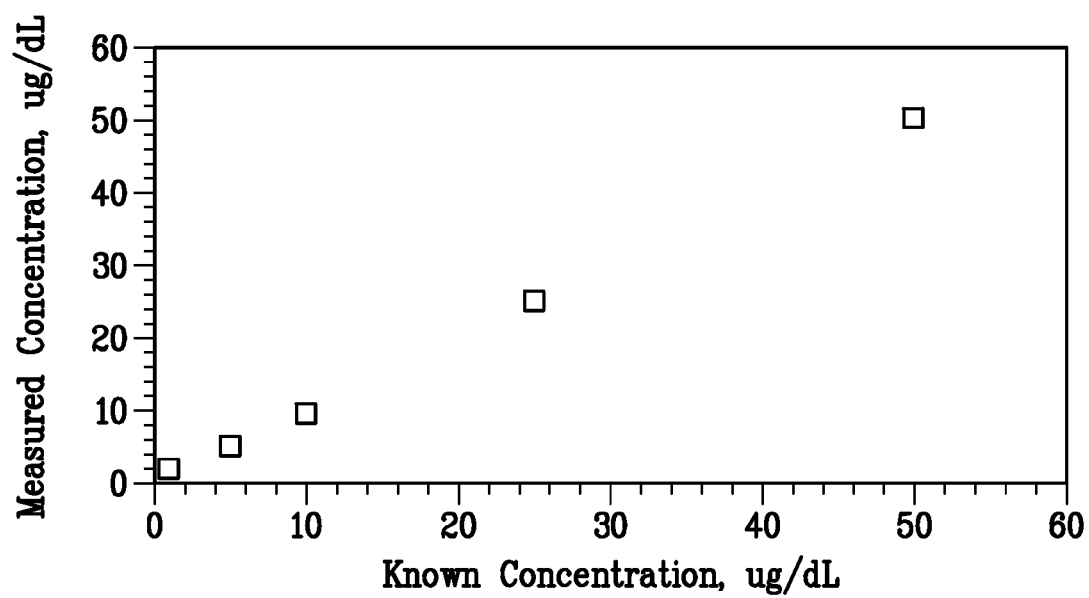
FIG. 1 shows the results of a linearity determination of a lead standard using inductively couples plasma-mass spectrometry (ICP-MS). A sample size of 7 was run in triplicate (total n=21) at each of the following concentrations: 0.1, 0.5, 1.5, 10, 25, and 50 µg/dL. $R^2=0.9999\pm0.0001$.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "heavy metal" and "toxic metal" are used interchangeably herein, and refer to elements having a specific gravity that is at least 5 times the specific gravity of water (1 at 4° C.). "Metalloids" are elements having both metal and non-metal characteristics. Non-limiting examples of heavy metals include antimony, arsenic, beryllium, bismuth, cadmium, cerium, chromium, cobalt, copper, gallium, gold, iron, lead, manganese, mercury, nickel, platinum, silver, tellurium, thallium, tin, vanadium, and zinc. (Lide 1992; Lide, D. CRC Handbook of Chemistry and Physics, 73rd Edition 1992. Boca Raton, Fla.: CRC Press.)

The term "swab" refers to any device suitable for collecting oral fluid formed from an absorbent material. Preferably, the absorbent material is attached to a holder, but the term swab, as used herein, includes free standing devices made from absorbent material that may be placed completely adjacent to the gumline to absorb the oral fluid located therein.

"Oral fluid" as used herein refers to the liquid normally present in the region of the oral cavity anterior to the teeth and gumline. While oral fluid usually contains some saliva, only relatively small amounts of the secretions of the salivary glands are present, mixed with gingival crevicular fluid and other secretions from the musosal surfaces of the cheek and gums. Thus, oral fluid is more akin to an ultrafiltrate of the plasma than common saliva. Depending on the method employed to gather the oral fluid and the oral health of the subject from whom the sample is gathered, a sample may contain cells from the collection site and even small amounts of blood (including both blood cells and plasma).

As used herein, "measure" or "determine" refers to any qualitative or quantitative determinations.

Many chemicals and biomolecules present in blood serum can also be detected in saliva, although the concentration of such chemicals and biomolecules in saliva is much lower than the concentration in serum. It has been discovered in accordance with the present invention that heavy metals such as lead can be detected in the oral fluid, as defined above, and it has surprisingly been discovered that the concentration of heavy metals in the oral fluid closely correlates with the concentration of heavy metals in the blood. Oral fluid being distinct from saliva, it has also been unexpectedly determined that oral fluid is superior to saliva for purposes of detecting lead and correlating the concentration of lead in the oral fluid with the concentration of lead in the blood serum.

Accordingly, the invention features methods for determining whether a subject has been exposed to a heavy metal by assaying oral fluid from a subject and measuring the concentration of the heavy metal in the oral fluid. The methods can be used for detecting, monitoring, or quantifying exposure to a heavy metal. Use of oral fluid provides distinct advantages over the traditional use of blood serum. For example, oral fluid can be collected safely, rapidly and non-invasively, can be collected in a non-clinical environment, and can be collected at a lower cost relative to blood collection and analysis. Moreover, preservation of the sample may be much less burdensome with oral fluid than with whole blood, making the methods of the present invention much easier to perform in situations where refrigeration of samples is difficult or impractical.

In the methods of the invention, the subject can be any animal, and is preferably a mammal such as a human, mouse, rat, cat, dog, horse, cow, donkey, sheep, or pig. Humans are most preferred.

In some aspects, the methods comprise providing a sample of oral fluid from the subject. The oral fluid can be obtained by any means suitable in the art. For example, various oral fluid collection devices and kits are known in the art and are commercially available. The oral fluid collection device can be comprised of or otherwise shaped or formed as particles, fibers, plates, and the like. Oral fluid can be collected by aspiration or absorption.

In some preferred aspects, the oral fluid is obtained by means of a swab. The swab can be comprised of any material suitable in the art such as alginate, sponge, capillary matrix, filter paper, calcium fibers, cellulose-based materials, or synthetic polymers such as a polyurethane, polyester, rayon, or a polymer of ethylene glycol and terephthalic acid. Polymers of ethylene glycol and terephthalic acid (i.e., polyethylene terephthalate) sold under the trade name DACRON® (DuPont) are particularly suited to the present invention. It is preferred that the swab not contain cotton or other natural cellulose-based materials, because cotton may be contaminated with metals from the soil in which the cotton plant was grown, thereby potentially contaminating the assay and producing inaccurate or false positive results. The absorbent material of the swab can be impregnated with salts or a hypertonic solution to facilitate absorption. The absorbent material can also be impregnated with a flavorant to make the sampling more pleasant to the subject. The swab can be on the end of a holder or an applicator made from plastic, wood, aluminum, and the like, with synthetic materials such as plastic being preferred The time required to collect oral fluid from the subject can vary. In some aspects, the oral fluid collection device is to remain in the subject's mouth for at least about 5 seconds, preferably at least about 10 seconds, more preferably at least about 15 seconds, and more preferably at least about 20 seconds, and more preferably at least about 20 seconds. In some aspects, the oral fluid collection device can remain in the subject's mouth for at least about 1 minute, or more.

The oral fluid can be obtained in a clinical or laboratory setting, and can be obtained from the upper jaw, lower jaw, or both, and can be obtained from the front or back of the mouth, or both. Preferably, the fluid is collected from the vestibular surface (either buccal or labial portions, or both) of the gumline (i.e., the line of interface between the gums and the teeth) of either the upper or lower dental arcade. Collection from the lower dental arcade (i.e. along the mandibular gumline) is preferred. The oral fluid can also be obtained from the space between the teeth and the gums.

Oral fluid can preferably be collected by moving the collection device back and forth, including with a swirling motion, along the gumline between the front and back of the mouth, or between the left and right sides of the mouth. Since it is preferable that the percentage of gingival crevicular fluid in the oral fluid be high, the amount of saliva in the oral fluid should be kept to a minimum. Thus, collection procedures that stimulate saliva production should be avoided. Such techniques are well known to those of skill in the art.

The oral fluid sample can be analyzed shortly after collection, or can be stored for later analysis. The oral fluid sample may also be frozen for long-term storage. Upon long-term storage, a suitable preservative or stabilizer can be added to the oral fluid sample, so long as the preservative or stabilizer does not introduce heavy metal contamination in a way that would skew the analysis. The sample can be analyzed with the oral fluid in its liquid form, or the sample can be dried prior to analysis. Dried samples can be stored indefinitely.

The oral fluid is analyzed to determine the concentration of a heavy metal present in it. The inventive methods can be used to determine the concentration of any heavy metal. Heavy metals of the greatest interest include mercury, lead, zinc, cadmium, chromium, vanadium, and arsenic. Lead is particularly preferred.

Determining the concentration of a heavy metal in the oral fluid can be accomplished by any means suitable in the art. It is preferable that the chosen means be sufficiently sensitive such that small quantities of the heavy metal in the oral fluid can be accurately detected and measured. Inductively coupled plasma mass spectrometry (ICP-MS) is one preferred sensitive technique suitable to measure the quantity of heavy metal in the oral fluid sample. Other techniques for analyzing the oral fluid include atomic absorption spectrometry, atomic emission spectroscopy, electrospray ionization tandem mass spectrometry, high performance liquid chromatography tandem mass spectrometry, inductively coupled plasma optical emission spectroscopy, and capillary zone electrophoresis mass spectrometry.

ICP-MS is a very powerful tool for trace (ppb-ppm) and ultra-trace (ppq-ppb) elemental analysis. ICP-MS is rapidly becoming the technique of choice in many analytical laboratories for the accurate and precise measurements needed for today's demanding applications. In ICP-MS, a plasma or gas consisting of ions, electrons and neutral particles is formed from Argon gas. The plasma is used to atomize and ionize the elements in a sample. The resulting ions are then passed through a series of apertures (cones) into the high vacuum mass analyzer. The isotopes of the elements are identified by their mass-to-charge ratio (m/e) and the intensity of a specific peak in the mass spectrum is proportional to the amount of that isotope (element) in the original sample.

In some aspects, the analysis of the sample may provide an accurate, quantitative measure of the amount of a particular heavy metal, such as lead, in the sample. Alternatively, the analysis may comprise correlating the concentration of said heavy metal in the sample with the amount of said heavy metal in the subject. Correlating may comprise comparing the concentration measurements with reference values for no exposure to the heavy metal, low level of exposure to the heavy metal, moderate level of exposure to the heavy metal, or high level of exposure to the heavy metal. The measured concentration values relative to the reference values indicates the level of the heavy metal in the blood of the subject.

Although any particular heavy metal may be sequestered in the body of a subject, a quantitative measure of the concentration of the heavy metal in a sample of oral fluid preferably provides as accurate an indicator of heavy metal exposure (also referred to herein as "heavy metal intoxication") as the concentration of heavy metal in the blood a subject. Indeed, since the heavy metal in the blood is often indicator of the amount of lead in the body that is free to interact chemically and cause adverse effects, in some instances, an assay of the heavy metal in the blood may be of greater value to the investigator than a "total-body" heavy metal measurement. Thus, since measurement of the concentration of a particular heavy metal in the oral fluid of a subject is closely correlated with the concentration of said heavy metal in the blood of said subject, the methods of the present invention generally provide as reliable indicator of heavy metal exposure as do methods that rely on an analysis of a sample of blood from a subject.

Accordingly, in another aspect, the methods of the present invention may provide a method of determining (or predicting) the concentration of a heavy metal in the blood of a subject. Such methods comprise providing a sample of the oral fluid of the subject, analyzing the sample to determine the concentration of said heavy metal in the sample. Since, as disclosed herein, the concentration of the heavy metal in the oral fluid is highly predictive (i.e. with a high confidence interval) of the concentration of the heavy metal in the blood, analysis of the oral fluid may be used as a preferable surrogate for analysis of the blood. In some aspects, the methods are predictive of the concentration of a heavy metal in a subject's blood with a confidence interval of about 75%. It is preferred that the methods are predictive of the concentration of a heavy metal in a subject's blood with a confidence interval of at least about 80%. More preferably, the confidence interval is at least about 83%, even more preferably at least about 85%, even more preferably at least about 88%, still more preferably at least about 90%, and still more preferably greater than at least about 91%, more preferably, the confidence interval is greater than about 92%, more preferably, the confidence interval is greater than about 93%, more preferably, the confidence interval is greater than about 94%, more preferably, the confidence interval is greater than about 95%, more preferably, the confidence interval is greater than about 96%, more preferably, the confidence interval is greater than about 97%, more preferably, the confidence interval is greater than about 98%, more preferably, the confidence interval is greater than about 99%.

Repeated measurements under identical conditions will result in a normal (Gaussian distribution about a mean. Measurements are considered sufficiently accurate is 95% of the measured values are within 2 standard deviations (±2σ) and 99% are within 3 standard deviations (±3σ). Measurements can be reported within a confidence defined by the standard deviation. For example if the mean measurement is 1 ug/dL and the standard deviation is 0.01 the 95% confidence interval reported value would be 1±0.02 ug/dL. Data may also be assessed based on the associated standard error of the mean which is calculated as the standard deviation divided by the square root of the number of values (measurements). The data can also be reported with a confidence interval expressed as the mean value±ts/sqrt n where t is the Student-t value for the number of samples, n, and s is the standard deviation. The instrument (ICP-MS) reports mean concentrations based on 3 replicate analyses of the same sample and an associated relative standard deviation (also known as coefficient of variation), which is defined as the standard deviation divided by the mean. Oral fluid metal concentrations can be reported as concentration± confidence interval.

Also featured in the invention are kits for determining the concentration of a heavy metal such as lead in the oral fluid. The kits comprise an oral fluid collection device such as a swab, and instructions for using the kit in a method for determining the concentration of heavy metals in oral fluid.

The following examples are provided to describe the invention in greater detail. They are intended to illustrate, not to limit, the invention.

Example 1

Determination of the Weight Variability in Polyester Swabs

In a preferred method of analyzing heavy metal concentration in an oral fluid sample, the swabs are dried prior to analysis. Drying of the swab prior to analysis eliminates extent of evaporation as a variable. According to this technique, the swab is separated from the holder at the base of the swab material, dried, then weighed using a high accuracy analytical balance. The mass of a corresponding blank swab is then subtracted from mass obtained, to determine the mass of sample in the swab.

It is thus important to select swabs that are of a consistent mass, at least within a particular manufacturing lot. One swab that meets the requirements of this analytical method is marketed by Copan Innovation. The dry weight of these sterile ethylene glycol/terephthalic acid swabs was determined using an analytical balance that is accurate to $10^{-4}$ grams. Ninety four swabs were weighed, and determined to have an average mass of 0.0934 g, with a standard deviation calculated to be 0.0033. Thus, very little variation in the mass of this brand of swab was observed.

Prior to analysis, the swabs are digested. The purpose of digestion is to reduce interference by organic matter and to convert metals associated with particulates to a form (usually the free metal ion) that can be measured by inductively-coupled plasma spectrometry (ICP-MS). Because digestion will add metals to the samples and blanks, minimal volumes of acids are used. A microwave digestion procedure can be used as an alternative. The microwave method is a closed-vessel procedure and thus provides improved precision.

Oral Fluid samples are prepared on a weight basis. Thus, acid blanks are prepared in parallel for each type of digestion performed. Although it is always best to eliminate all relevant sources of contamination, a reagent blank prepared with the same acids and subjected to the same digestion procedure as the sample can correct for impurities present in acids and reagent water.

Example 2

Calibration of Inductively Couple Mass Spectrometer for Metal Analysis

For ICP-MS, sample material is introduced into an argon based, high-temperature radio-frequency plasma, usually by pneumatic nebulization. Energy transfer from the plasma to the sample stream causes desolvation, atomization, and ionization of target elements. Ions generated by these energy-transfer processes are extracted from the plasma through a differential vacuum interface, and separated on the basis of their mass-to-charge ratio by a mass spectrometer. The mass spectrometer usually is of the quadrupole or magnetic sector type. The ions passing through the mass spectrometer are counted, usually by an electron multiplier detector, and the resulting information processed by a computer-based data-handling system. This method is suitable for aluminum, antimony, arsenic, barium, beryllium, cadmium, chromium, cobalt, copper, lead, manganese, molybdenum, nickel, selenium, silver, strontium, thallium, uranium, vanadium, and zinc, among others.

Instrumentation, available from several manufacturers, includes a mass spectrometer detector, inductively coupled plasma source, mass flow controllers for regulation of ICP gas flows, peristaltic pump for sample introduction, and a computerized data acquisition and instrument control system. An x-y autosampler also may be used with appropriate control software. For analyses, precleaned plastic laboratory ware is used for standard and sample preparation. Teflon, either tetrafluoroethylene hexafluoropropylene-copolymer (FEP), polytetrafluoroethylene (PTFE), or perfluoroalkoxy PTFE (PFA) is preferred for standard preparation and sample digestion, while high-density polyethylene (HDPE) and other dense, metal-free plastics may be acceptable for internal standards, known-addition solutions, and the like.

All metals analyses using ICP-MS are calibrated prior to each batch of analyses being performed. The instrument is calibrated with a minimum of one blank and five standards. In the case of lead analysis, the standards consist of five concentrations between 1 and 10 parts per billion. Based on the standard measurements, a regression line can be generated along with an R-squared (Rsq) value. It is preferred that the lower confidence limit based on the standard error of the Rsq value be 0.995.

An example of linearity determination for lead is shown in FIG. 1. Seven samples were run in triplicate at the following concentrations: 0.1, 0.5, 1.5, 10, 25, and 50 µg/dL, using a dynamic reaction cell inductively coupled plasma mass spectrometer (DRCII). Linearity was determined to be 0.99972, 0.9984, and 0.9992 for each respective experiment. Analyses demonstrated less than 5% intra-assay, and less than 10% inter-assay variation. Rsq was calculated to be 0.9999±0.0001. Table 1 below shows the variance between days showing that the instrument is stable between days and between runs on a single day.

TABLE 1

Stability of inter-day variance between ICP-MS samples of known concentrations.

| Known Concentration (µg/dL) | 1.0 µg/dL | 10 µg/dL |
|---|---|---|
| Day 1 | 1.1 | 10.12 |
|  | 0.98 | 9.87 |
|  | 1.02 | 10.12 |
|  | 1.05 | 9.99 |
|  | 0.97 | 10.09 |
|  | 1.01 | 9.95 |
|  | 1.02 | 10.05 |
| Day 2 | 0.88 | 9.43 |
|  | 1.01 | 10.01 |
|  | 0.97 | 9.74 |
|  | 1.03 | 9.96 |
|  | 1.01 | 9.96 |
|  | 1.00 | 10.03 |
|  | 0.98 | 9.84 |
| Day 3 | 1.05 | 9.73 |
|  | 1.04 | 9.93 |
|  | 1.03 | 9.69 |
|  | 0.96 | 9.76 |
|  | 1.04 | 10.23 |
|  | 1.02 | 10.16 |
|  | 1.0 | 9.69 |
| Mean | 1.01 | 9.92 |
| S.D. | 0.04 | 0.19 |
| CV | 4.39 | 1.96 |
| Accuracy | 99.19 | 99.22 |

For quality control purposes, the calibration blank is run followed by a linearity standard to determine linearity in the concentration range. An independent calibration verification standard is run next as a check on the calibration standards. An interference check standard is then run. When all analyses meet the acceptance criteria, sample analyses are begun. After every 10 samples and at the end of a run, a continuing calibration blank and a continuing calibration verification standard are run. Results outside of the established criteria trigger reanalysis of samples analyzed from the last acceptable check standard. A calibration curve is prepared with a minimum of a calibration blank and five standards, and then verified with a standard from a certified source. The calibration is verified on an ongoing basis with a quality control check standard. If this standard does not meet established acceptance criteria (±10% midrange), the system is recalibrated and all samples analyzed since the last acceptable check are reanalyzed.

Example 3

Analysis of Oral Fluid Samples for the Presence of Lead

Dried Dacron® swabs from Copan Innovation, containing oral fluid samples, were excised from the handle at the proximal extent of the fibers and weighed. The mass of blank swabs from the same lot were subtracted, to determine the dry weight of the sample. The sample swabs were then each dissolved in 1 ml of nitric acid, and diluted to a final volume of 15 ml with 18 megaohm deionized water, to which indium ($^{115}$In) was added to a concentration of 20 parts per billion. An unused swab was prepared in parallel to serve as a negative control. Samples were then assayed by ICP-MS on a Perkin Elmer Elan Dynamic Reaction Cell™ II ICP-MS or a PerkinElmer ELAN 9000 ICP-MS.

Figure 2:
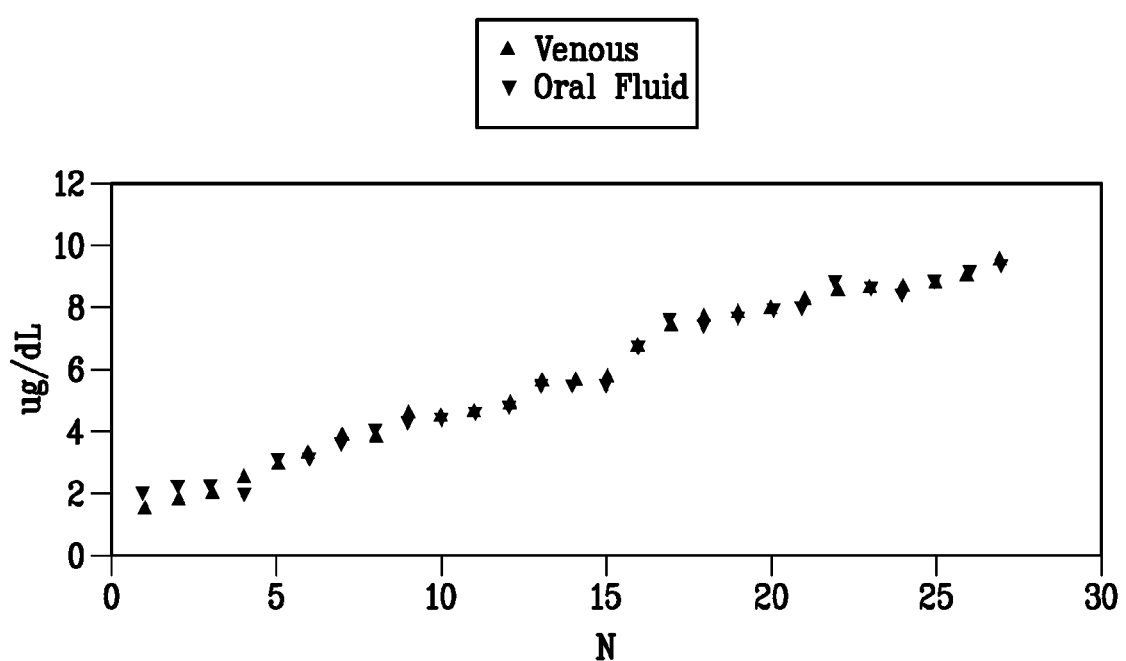
FIG. 2 shows the correlation of the concentration of lead in oral fluid with the concentration of lead in blood serum. Twenty three pairs of samples were analyzed by ICP-MS for oral fluid lead and blood lead for each patient.

As a pilot experiment, patient samples of oral fluid and blood were analyzed using inductively couple plasma mass spectrometry to determine the concentration of lead in each respective biological fluid. Statistical analyses were carried out to determine whether the level of lead in each fluid could be correlated. The results are provided in FIG. 2. Ninety five children were tested for lead (mean 3.3 mg/dL+1.3 mg/dL, range 3 mg/dL–45 mg/dL). The correlation between oral fluid and blood lead concentration was significant (0.879, p<0.05). Of twenty one test between 3 mg/dL and 10 mg/dL, the correlation was 0.938 (p<0.001, two tailed) between blood and oral fluid.

Example 4

Detailed Analysis of Oral Fluid Samples for the Presence of Lead

This prophetic example describes how the inventive oral fluid assays for lead exposure can be evaluated for their ability to correlate with blood assays for lead exposure.

A study of 500 children meeting eligibility criteria as defined below will be enrolled in this study. The study will enroll children of any sex, aged from 9 months to six years old, who received care from Children's Healthcare of Atlanta at Hughes Spalding Pediatric Appointment Clinic and Pediatric Emergency Clinic. This facility was chosen because it serves a high proportion of low income and minority children, groups that are at a higher risk for lead poisoning. Informed consent will be obtained from the parents or legal guardians of all children prior to their enrollment in the study. Oral fluid, urine, and blood will be sampled and analyzed.

Exclusion criteria for this study will include: less than 9 months of age, greater than 6 years of age, lack of parental consent, inability to obtain a venous blood sample, and current treatment or chelation therapy for lead poisoning.

Oral fluid will be obtained using a DACRON® (DuPont) swab, with the specimen collector placing the swab into the well of the mouth between the teeth and the lips, preferably in the lower jaw. The swab will be moved gently from back to front of the mouth for at 15 seconds. The swab will then be placed into a sterile tube, and secured with a cap on the tube. Tubes will be properly labeled and sealed with a tamper-evident seal.

Urine samples will be collected in a sterile specimen collection bottle by means of a voluntary void. The sample will be secured with a tamper-evident cap. The collection bottle will then be gently shaken to ensure there are no leaks. Secured bottles will be labeled with the subject's information.

Venous blood will be collected in accordance with accepted protocols. In brief, a tourniquet will be used and released as appropriate, and the vein will be accessed using vacuum containers, and in a manner that will cause minimum discomfort to the subject. After the sample is collected, blood flow will be stopped using sufficient pressure for a sufficient length of time to ensure that bleeding has stopped. A suitable dressing will be applied to the puncture site, and the subject and parent will be advised of how to care for the site. Samples will be labeled and secured.

Oral fluid, urine, and venous blood samples will be analyzed to determine the presence of lead. This analysis will proceed using any means that are suitable and acceptable in the art.

The present invention is not limited to the embodiments described and exemplified above, but is capable of variation and modification within the scope of the appended claims.

What is claimed:

1. A method of assaying a subject for heavy metal exposure, comprising providing a sample of oral fluid from a subject, said sample obtained by contacting the gumline of the subject, and measuring the concentration of said heavy metal present in said sample.

2. The method of claim 1, wherein the subject is a human.

3. The method of claim 1, wherein providing the sample comprises providing a swab comprising the subject's oral fluid.

4. The method of claim 3, wherein providing the swab comprises rubbing the swab along the vestibular aspect of the mandibular gumline.

5. The method of claim 3 wherein the swab comprises a polymer of ethylene glycol and terephthalic acid.

6. The method of claim 3 further comprising digesting the swab using acid or microwave radiation.

7. The method of claim 1, wherein said measuring step utilizes inductively coupled plasma mass spectrometry.

8. The method of claim 1, wherein the heavy metal is lead.

9. The method of claim 8, wherein said concentration of lead in said sample is predictive of the amount of lead in the blood of said subject with a confidence interval of greater than 90%.

10. The method of claim 9 wherein said concentration of lead in said sample is predictive of the amount of lead in the blood of said subject with a confidence interval of greater than 95%.

11. The method of claim 10 wherein said concentration of lead in said sample is predictive of the amount of lead in the blood of said subject with a confidence interval of greater than 98%.

12. The method of claim 11 wherein said concentration of lead in said sample is predictive of the amount of lead in the blood of said subject with a confidence interval of greater than 99%.

13. The method of claim 1, wherein the heavy metal exposure is intoxication.

14. The method of claim 13, further comprising the step of correlating the concentration of said heavy metal in said sample with the concentration of said heavy metal in said subject.

15. The method of claim 14, wherein said correlating step comprises comparing the concentration measurement with reference values for no exposure to the heavy metal, low level of exposure to the heavy metal, moderate level of exposure to the heavy metal, or high level of exposure to the heavy metal; said measurement relative to the reference values being indicative of the level of the heavy metal in the blood of the subject.

16. A method for predicting the concentration of a heavy metal in the blood of a subject, comprising providing a sample of oral fluid from the subject, said sample obtained by contacting the gumline of said subject, determining the concentration of the heavy metal in the oral fluid, wherein the concentration of said heavy metal in the oral fluid is predictive of the concentration of said heavy metal in the blood of the subject.

17. The method of claim 16, wherein the subject is a human.

18. The method of claim 16, wherein the heavy metal is lead.

19. The method of claim 16, wherein the step of providing a sample of oral fluid comprises rubbing a swab along the vestibular aspect of the subject's mandibular gumline.

20. The method of claim 19, wherein the swab comprises a polymer of ethylene glycol and terephthalic acid.

21. The method of claim 19 further comprising digesting the swab using acid or microwave radiation.

22. The method of claim 16, wherein the step of determining comprises the use of inductively coupled plasma mass spectrometry.

23. A system for providing a quantitative assessment of heavy metal intoxication, said system comprising a sample of oral fluid from a subject obtained by contacting the gumline of a patient and means for measuring the amount of said heavy metal in said sample.

24. The system of claim 23 wherein said means for measuring the amount of said heavy metal in said sample comprises inductively coupled plasma mass spectrometry.

25. The system of claim 23, wherein said heavy metal is lead.

26. The system of claim 23, wherein said sample comprises oral fluid on a swab.

27. The system of claim 26, wherein said swab comprises a polymer of ethylene glycol and terephthalic acid.

\* \* \* \* \*